United States Patent
Mei et al.

(10) Patent No.: US 9,757,327 B2
(45) Date of Patent: Sep. 12, 2017

(54) ABUTILON INDICUM EXTRACTS AND METHODS OF USE

(71) Applicant: Avon Products, Inc., Suffern, NY (US)

(72) Inventors: Bing C. Mei, Mahwah, NJ (US); John W. Lyga, Basking Ridge, NJ (US)

(73) Assignee: Avon Products, Inc., Rye, NY (US)

( * ) Notice: Subject to any disclaimer, the term of this patent is extended or adjusted under 35 U.S.C. 154(b) by 0 days.

(21) Appl. No.: 14/767,609

(22) PCT Filed: Feb. 28, 2014

(86) PCT No.: PCT/US2014/019213
§ 371 (c)(1),
(2) Date: Aug. 13, 2015

(87) PCT Pub. No.: WO2014/158671
PCT Pub. Date: Oct. 2, 2014

(65) Prior Publication Data
US 2015/0374619 A1    Dec. 31, 2015

Related U.S. Application Data

(60) Provisional application No. 61/783,274, filed on Mar. 14, 2013.

(51) Int. Cl.
*A61K 36/00* (2006.01)
*A61K 8/97* (2017.01)
*A61Q 19/00* (2006.01)
*A61Q 19/02* (2006.01)
*A61Q 19/08* (2006.01)

(52) U.S. Cl.
CPC ............... *A61K 8/97* (2013.01); *A61Q 19/00* (2013.01); *A61Q 19/02* (2013.01); *A61Q 19/08* (2013.01)

(58) Field of Classification Search
None
See application file for complete search history.

(56) References Cited

U.S. PATENT DOCUMENTS

2013/0309181 A1    11/2013    Boulet et al.

FOREIGN PATENT DOCUMENTS

| CN | 102743499 A | 10/2012 | |
|---|---|---|---|
| JP | 06329545 A | * 11/1994 | |
| WO | 9834591 A1 | 8/1998 | |
| WO | WO 0166080 A1 | * 9/2001 | ............. A61K 8/342 |
| WO | 2011127559 A1 | 10/2011 | |
| WO | 2012131723 A1 | 10/2012 | |

OTHER PUBLICATIONS

Shanthi et al, Pharmacognosy, analysis of bio-active compounds from Abutilon indicum Linn. (Malvaceae) by using gas chromatography and mass spectrometry (GC-MS) in ethanol and hexane solvent. Journal of Pharmacy Research (2011), vol. 4, No. 12, pp. 4795-4797.*

Kashmiri, MA et al., "Characterization, Compositional Studies, Antioxidant and Antibacterial Activities of Seeds of Abutilon indicum and Abutilon indicum Grown Wild in Pakistan," Acta Chim. Slov, vol. 56, pp. 345-352 (2009).

Mangla, M. et al., "Review on Pharmacological Activities of Tranditional Medicine: Abutilon indicum," Int. J. Pharm. Ed. Appl. Sci, vol. 1, No. 2, pp. 29-43 (2012).

* cited by examiner

*Primary Examiner* — Qiuwen Mi
(74) *Attorney, Agent, or Firm* — Brian P. McCloskey; Elizabeth M. Morters

(57) ABSTRACT

Methods of using extracts of *Abutilon indicum* to impart benefits to skin and/or improve skin conditions resulting from aging or damaged skin.

2 Claims, 1 Drawing Sheet

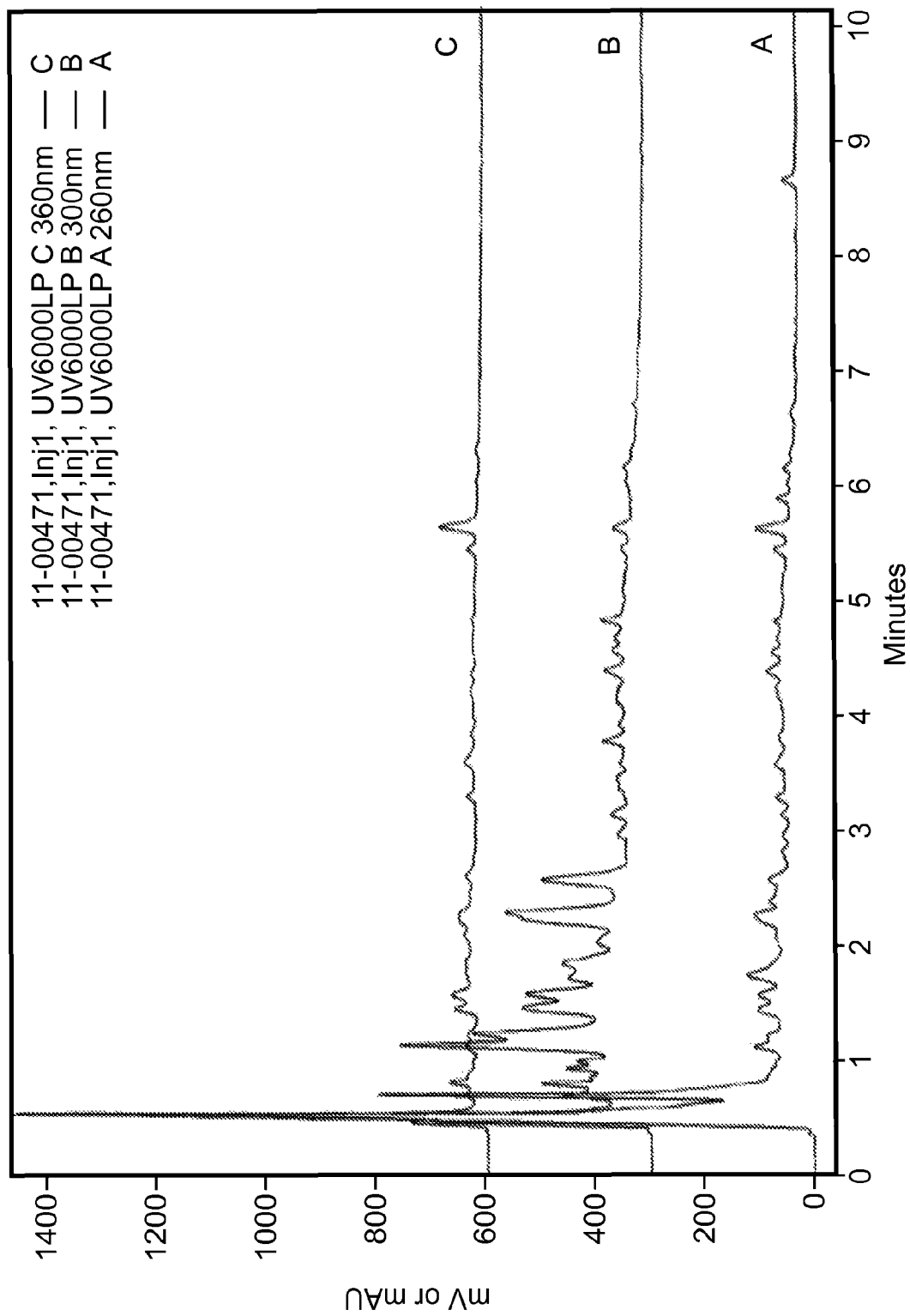

ABUTILON INDICUM EXTRACTS AND METHODS OF USE

CROSS-REFERENCE TO RELATED APPLICATIONS

This patent application is a National Phase application of International Application No. PCT/US2014/019213, filed Feb. 28, 2014, and claims priority to United States Patent Application Serial No. 61/783,274, filed Mar. 14, 2013. The entirety of the aforementioned applications are incorporated herein in their entirety by reference.

FIELD OF INVENTION

The present invention relates generally to compositions for topical application to the skin which comprise extracts of *Abutilon indicum* and the use of such compositions to provide benefits to the skin, in particular, aesthetic improvement, anti-aging, anti-cellulite, skin lightening, and/or anti-wrinkle benefits.

BACKGROUND OF THE INVENTION

Human skin is broadly divided into two layers: the surface epidermis which provides an anatomical barrier to foreign elements and maintains the body's internal environment, and the underlying dermis which provides nutritional and structural support to the epidermis. The epidermis consists of a keratinized stratified squamous epithelium comprising four types of cells: keratinocytes, melanocytes, Merkel cells, and Langerhans' cells, with the majority of epidermal cells being keratinocytes. It is comprised of several sub-layers (from the innermost outwards): *Stratum germinativum/Stratum basale, Stratum spinosum, Stratum granulosum*, and *Stratum corneum*. The keratinocytes, generated by the mitosis of keratinocyte stem cells, originate in the stratum basale and then push up through the strata. As these cells move to the surface of the skin they undergo gradual differentiation, becoming anucleated, flattened, and highly keratinized. During this process the keratinocytes become highly organized. They form desmosomes, cellular junctions, between each other and, through the excretion of keratin proteins and lipids, form an extracellular matrix which strengthens the skin. Eventually the keratinocytes die off and form the stratum corneum. The epidermis provides waterproofing and serves as a barrier to infection and other external elements. In normal and healthy skin, keratinocytes are shed and replaced continuously every 30 days. In aging skin, the stratum corneum loses its capacity to retain moisture as the rate of keratinocyte renewal is reduced, and the skin dehydrates.

Glycosaminoglycans (GAGs) are produced by the body to maintain structural integrity in tissues and to maintain fluid balance. GAGs serve as a natural moisturizer and lubricant between epidermal cells to inhibit the production of matrix metalloproteinases (MMPs)—enzymes activated by UV exposure or inflammation that contribute to the breakdown of collagen while inhibiting new collagen formation. Topical GAG stimulants, GAG supplements and/or MMP inhibitors can help to provide temporary restoration of enzyme balance to slow or prevent matrix breakdown and consequent onset of wrinkle formation.

Hyaluronic acid (HA) is a type of GAG that promotes collagen synthesis, repair, and hydration and is a major component of the epidermis, where it is involved in tissue repair. When skin is exposed to excessive UVB rays, it becomes inflamed (sunburn), the cells in the dermis stop producing as much hyaluronic acid, and HA degradation rates increase. HA degradation products then accumulate in the skin after UV exposure. HA plays an important role in the normal epidermis. In normal skin, HA is found in relatively high concentrations in the basal layer of the epidermis where proliferating keratinocytes are found. Maintaining the extracellular space and providing an open, as well as hydrated, structure for the passage of nutrients are the main functions of HA in epidermis. HA content increases in the presence of retinoic acid (vitamin A). The proposed effects of retinoic acid against skin photo-damage and aging may be correlated, at least in part, with an increase of skin HA content, giving rise to an increase in tissue hydration. Epidermal HA also functions as a manipulator in the process of keratinocyte proliferation, which is essential in normal epidermal function, as well as during reepithelization in tissue repair. Decrease in skin elasticity, impaired local inflammatory response, and impaired tissue repair may result from a decrease in HA levels. Thus, HA stimulators may contribute to anti-aging effects on and/or improvement in aesthetic appearance of skin.

The dermis is the underlying layer of the skin located between the epidermis and subcutaneous tissue. It is the thickest of the skin layers and comprises the extracellular matrix (ECM) of the skin, which is maintained by fibroblast cells and comprised of collagen, elastin, and other components. Fibroblasts maintain the structural integrity of the dermis by continuously secreting precursors of the extracellular matrix. In the aging skin, the fibroblasts ensure a balance between the synthesis and maturation of both the collagen and elastin fibres. Fibroblast senescence tips this equilibrium towards the breakdown of collagen and elastin fibres and other ECM components.

Collagen and elastin are the major components of the dermal-epidermal junction (DEJ), i.e., a specialized structure mediating close contact between the lamina densa and the underlying connective tissue of the dermis at the basement membrane zone between the epidermis and dermis. The dermal-epidermal junction (DEJ) includes interlocking fingerlike projections called Rete ridges. The cells of the epidermis receive their nutrients and oxygen from the blood vessels in the dermis because the epidermis does not have its own blood vessels. The Rete ridges at the DEJ increase the surface area of the epidermis that is exposed to the dermis, so that the uptake of necessary nutrients/oxygen is more efficient, and the two layers of skin can bind more strongly and resist mechanical stress. The DEJ flattens out with aging, such that the skin is more fragile and more likely to shear. This process also decreases the amount of nutrients/oxygen available to the epidermis by decreasing the surface area of the epidermis in contact with the dermis, thereby interfering with the skin's normal repair process. As a result, the skin shows signs of aging such as fragility, lines and wrinkles, sagging, dull, discoloration, and uneven tone, rough texture, and the like.

The main structural component of the dermis is also collagen. Bundles of collagen molecules pack together throughout the dermis, accounting for three-fourths of the dry weight of skin. Procollagen is the precursor molecule of collagen, synthesized in the fibroblast, osteoblast, etc., and cleaved to form collagen extracellularly. Collagen has great tensile strength, and along with soft keratin, is responsible for skin strength and elasticity. As aging occurs, the production of collagen is reduced, while the degradation is accelerated due to an overproduction of collagenase, i.e., protease that breaks down collagen. Collagen deficiency may lead to reduction in skin strength and elasticity, which in turn may lead to wrinkles, sagging, and fragility of the aging skin. For a more detailed background on collagen, see Lodish, et al. Molecular Cell Biology, W.H. FREEMAN, New York, N.Y. 4.sup.th edition, 2000, the disclosures of which is incorporated herein by reference. Thus, it is anticipated that the retention of or stimulation of collagen and/or procollagen production and/or the reduction in production of collagenase would provide for a healthier and stronger skin, thereby reducing wrinkles, sagging, and fragility of the aging skin.

Elastin is a protein that allows the skin to stretch and recoil to its original state. It is found in both the ECM and the dermis layer of the skin. Elastin polymers are formed by the cross-linking of tropoelastin monomers. Although there are as many as five enzymes that can catalyze this process, it is unclear exactly how the crosslinking is regulated. Elastin is not believed to be produced past puberty, after which maintenance of the elastin polymers in tissue is regulated by competing activities of renewing (e.g., "anti-elastase") and degrading (e.g., elastase) mechanisms. As one ages, an imbalance in the competing activities occurs, which results in a loss of elasticity in elastin-containing tissues. This loss of elasticity in skin can appear as wrinkles in the surface of the skin.

Thus, the successful restoration of youthful skin from this perspective must address a variety of key issues including: vitality of fibroblasts and keratinocytes, cell-cell adhesion in the epidermis and dermis, cell nourishment to the epidermis, cell-cell anchoring and adhesion between keratinocytes, communication between the dermis and epidermis, collagenase overproduction, collagen replacement, and mechanical properties of the skin. Any natural plant material, including an extract derived therefrom, that addresses these key issues is useful in the topical composition of the present disclosure.

While the keratinocytes are within the stratum basale they acquire melanin, a black ultraviolet light absorbing pigment, from melanocytes. Melanocytes produce melanin within organelles known as melanosomes and then transfer the melanin containing melanosomes to neighboring keratinocytes via their dendrites. Within each keratinocyte the melanosomes form a melanin cap which is retained within the keratinocyte until the keratinocyte is shed from the skin. The melanin cap reduces ultra-violet-induced DNA damage to the human epidermis and the underlying cells and tissues. Melanin provides the skin with its color and thus the intensity of skin color is directly related to the number, size, melanin content, rate of formation, and rate of keratinocyte transfer of melanosomes, as well as the , rate at which melanin degrades within keratinocytes. For a more detailed background on melanin, see G. Costin and V. Hearing, "Human skin pigmentation: melanocytes modulate skin color in response to stress," The FASEB Journal Vol. 21, pages 976-994, April 2007, the disclosure of which is incorporated herein by reference in its entirety. The synthesis of melanin is a complex process involving several biochemical pathways. Some skin lighteners or depigmenting agents, such as hydroquinone and kojic acid, act as inhibitors of tyrosinase, an enzyme that has its catalytically active domain within organelles known as melanosomes. Tyrosinase converts phenols, including tyrosine, to ortho-quinones which are subsequently converted to melanin within the melanosomes. Other skin lighteners, such as serine-protease inhibitors, act by disrupting the transfer of the melanosomes from melanocytes to the keratinocytes.

Cellulite is the lumpy uneven type of subcutaneous fat that tends to accumulate on the buttocks, thighs, and limbs of many women. It is considered unsightly because it gives the tissues underlying the skin an "orange peel" or "cottage cheese" look. Compressing the skin, as when sitting or crossing the legs, produces a "mattress appearance" with bulging and pitting of the fatty layer. Nodules of fat may be felt trapped within hardened connective tissue. The histology of cellulite-affected skin indicates that cellulite results from a combination of enlarged fat tissue and weak dermal structure and connective tissue septa. Excess fat accumulation increases the volume of adipocytes, which bulge into a weakened dermis to create the characteristic irregularities in the appearance of the epidermal surface. A number of factors can cause cellulite including, e.g., hereditary, intestinal, circulatory, lymphatic, hormonal, and lifestyle factors. Dieting to decrease fat intake, exercising to increase fat metabolism and prevent the build up of cellulite, and massage and hydrotherapy to stimulate lymphatic drainage can help reduce the appearance of cellulite. Nonetheless, these means for combating cellulite or subcutaneous fat are limited, and the need remains for additional approaches. The protrusion of enlarged fat tissue into the dermis is one of the major factors contributing to the appearance of cellulite. One of the approaches to improve cellulite is to stimulate fat breakdown and reduce the amount of fat and/or lipids in the adipocytes, or fat cells.

There is active interest in the cosmetics industry in developing products that may be applied topically to the skin to counteract adverse changes in the skin. Cosmetic products that reverse or forestall such changes (including chronologically, environmentally, and/or physiologically-mediated changes) are increasingly in demand. Consumers continually seek to improve the appearance of their skin and in particular to reduce visible signs of skin aging. Unwanted signs include lines and wrinkles, skin sagging or atrophy, loss of suppleness, thickness, plumpness, tautness, elasticity, resiliency, and firmness, loss of cell growth, proliferation, and/or functionality in the epidermal and/or dermal skin layers, and there remains a need for products that combat such signs of aging and, more generally, that provide anti-aging and/or anti-wrinkle effects.

Consumers continually seek to improve the appearance of their skin, and in particular seek to improve the appearance of skin affected by unwanted deposition and/or accumulation of fat, including cellulite. There is active interest in the cosmetics industry to develop products that may be applied topically to the skin to provide anti-cellulite benefits, as well as other anti-lipid benefits. Cosmetic products that enhance the appearance of skin are increasingly in demand as consumers increasingly seek to mitigate and delay signs of excess accumulation and/or production of subcutaneous fat.

Numerous means for obtaining a white or pale complexion are known and include skin lightening creams, bleaches, peels, and oral and injectable medication. Many of the known active ingredients include kojic acid, ascorbic acid, hydroquinone, niacinamide, and glutathione, in addition to natural extracts, licorice, *Glycyrrhiza glabra*, arbutin, bearberry, *Chlorella vulgaris* extract, *Perilla* extract, and coconut fruit extract, as well as derivatives of any of the previously mentioned active ingredients. These and other known lightening products work in various ways. Some are based on inhibiting the production of melanin, which is responsible for pigmentation, e.g.,. thiodipropionic acid, such as described in US Patent Application Publication Serial No. 2004/0126344, herein incorporated in its entirety for all purposes. Others are acids that remove old skin by promoting exfoliation, for example, alpha hydroxyl acids.

Over the years, a variety of approaches for treating these skin irregularities have been offered. Numerous dermatologic creams, lotions, vitamins, and herbal supplements have been proposed. Further, private spas and salons have offered massages, scrubs, wraps, compresses, essential oils, and herbal products to address the irregular skin contours.

Safe, effective and new components of compositions to treat, reduce, inhibit and/or improve the dermatological signs of aging; improve skin aesthetic appearance; reduce cellulite; lighten skin; and/or treat wrinkles, would be advantageous in the formulation of treatments and products for the skin. As described herein, novel and beneficial methods and compositions, as well as their mode of action, for the treatment of wrinkles and the like, as well as for personal care products for the skin, are provided.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

BRIEF DESCRIPTION OF THE DRAWINGS

FIG. 1 depicts an HPLC profile of an exemplary butanol/water extract of *Abutilon indicum*.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, and some features may be exaggerated to show details of one embodiment components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Whenever a term is identified by reference to a range, the range will be understood to explicitly disclose every element thereof. As a non-limiting example, a range of 1-10% will be understood to include 1%, 2%, 3%, 4%, 5%, 6%, 7%, 8%, 9%, and 10%, and all values between 1 and 10%.

Where two or more substituents are referred to as being "independently selected from" a group of enumerated alternatives, it is meant that each substituent can be any element of that group, independent of the identity of the other substituents.

As used herein, "% by weight" or "% wt." refers to the weight percent of a component in relation to the total weight of the composition (i.e., including any carriers, vehicles, solvents, fillers, or other components added before application to the skin) unless otherwise provided.

All terms used herein are intended to have their ordinary meaning unless otherwise provided. For the purposes of describing and claiming the present invention, the following terms are defined:

"Anti-Aging Benefit" Anti-aging benefits include, but are not limited to, one or more of: (a) treatment, reduction, and/or prevention of fine lines or wrinkles, (b) reduction of skin pore size, (c) improvement in skin thickness, plumpness, and/or tautness; (d) improvement in skin suppleness and/or softness; (e) improvement in skin tone, radiance, and/or clarity; (f) improvement in procollagen and/or collagen production; (g) improvement in skin texture and/or promotion of retexturization; (h) improvement in skin barrier repair and/or function; (i) treatment and/or prevention of skin sagging or atrophy; (j) improvement in appearance of skin contours; (k) restoration of skin luster and/or brightness; (l) replenishment of essential nutrients and/or constituents in the skin; (m) improvement of skin appearance decreased by menopause; (n) improvement in skin moisturization and/or hydration; and (o) improvement of skin elasticity and/or resiliency.

"Anti-Cellulite Benefit" Anti-cellulite benefits include, but are not limited to, improving the appearance of skin affected by cellulite and/or combating signs of unwanted subcutaneous fat may include, without limitation, one or more of the following: reduction in appearance of cellulite lumpiness and/or unevenness; reduction in pitting appearance of cellulite upon squeezing; reduction in extent of area affected by cellulite; prevention or delay in recurrence of cellulite; prevention or treatment of acne; prevention or treatment of oily skin; reduction in subcutaneous fat deposition and/or accumulation; improvement in collagen deposition; and improvement in connective tissue strength.

"Anti-Lipid Agent" Anti-lipid agents include, but are not limited to, phosphodiesterase inhibitors; adenylate cyclase inhibitors; lipolysis stimulators; beta-adrenergic agonists; alpha-2-adrenergic receptor antagonists; xanthine analogues; forskolin; a forskholii extract; a hawthorne extract; a cola extract; isoprotenerol; yohimbine; Ginkgo bilboa extract; perilla oil; and combinations thereof.

"Antioxidant" means substances that function, among other things, to scavenge free radicals from skin to protect the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate, sodium ferulate); gallic acid derivatives (e.g., propyl gallate); [[lycopene; reductic acid; rosmarinic acid; tannic acid not used a lot]]; oxa acids, such as 3,6,9-trioxaundecanoic acid; tetrahydrocurcumin; tocopherol and its derivatives (e.g., tocopheryl acetate); or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

"Anti-Wrinkle Benefits": Anti-wrinkle benefits include, but are not limited to, reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; and/or reducing or preventing skin atrophy.

"Candidate Substance" The term "candidate substance" refers to any substance that is tested for activity, e.g., in or on or with a cell or other substrate, whether or not the substance is suspected of possessing such activity. In one embodiment, the cell I other test substrate is a dermal fibroblast or precursor thereof. In another embodiment, the cell is a human or mouse cell. After the cell has been incubated with a candidate substance for a sufficient length of time to provide a measurable change in expression levels, which will typically be at least one hour, and more typically from about 72 hours to 144 hours (3 to 6 days) it is then lysed to release the cellular components, such as mRNA encoding those proteins. The amount of mRNA, cDNA or any other resultant substance indicating relative expression may then be measured by any suitable technique for detection and quantitation of peptides and proteins and/or polynucleotides (e.g., mRNA).

"Chronologic Aging" The term "chronologic aging" means age of a person measured in years, months, and days from the date the person was born.

"Collagen And/Or Elastin Stimulator" means a candidate substance that stimulates the increased translation of or stability of a collagen and/ or elastin protein; and/or that upregulates production of mRNA encoding such a protein.

"Cosmetically Acceptable" By "cosmetically acceptable," it is meant that a particular component or composition is generally regarded as safe and non-toxic at the levels employed.

"Decreasing Melanin Synthesis" The term "decreasing melanin synthesis" and related expressions refer to reducing the amount of one or more of the different types of melanin biosynthesized in skin and/or deposited in hair, and in one embodiment refers to reducing melanocyte-mediated hyperpigmentation.

"Effective Amount" An "amount effective" or an "effective amount" to provide a particular benefit to the skin refers to the active amount of a candidate substance (absent other non-inert diluent, solvent, carrier, filler, other ingredient) sufficient to provide an improvement in the particular manifestation of skin when applied for a sufficient time. The effective amount of each substance when used in combination with another may be the same, greater than, or less than the effective amount of the substance when used alone. Use of lower amounts of individual substances is contemplated when used in combination with other active agents, e.g., due to synergistic effects in producing a clinically measurable improvement in a particular manifestation of skin.

"Expression Levels" As used herein, the term "expression levels" refers to an amount of a gene and/or protein that is expressed in a cell. As used herein, a "gene" includes a polynucleotide containing at least one open reading frame that is capable of encoding a particular polypeptide. As used herein, the terms "polynucleotide" is synonymous with "oligonucleotide" and includes polymeric forms of nucleotides of any length, either deoxyribonucleotides or ribonucleotides, or analogs thereof, including, without limitation, mRNA, DNA, cDNA, primers, probes, and the like.

"Improve Aesthetic Appearance" Improving the aesthetic appearance of skin includes, but is not limited to, one or more of: reduction in dermatotological signs of chronological aging, hormonal aging, and/or photoaging; reduction in skin fragility; reduction in pore size; prevention and/or reversal of loss of collagen and/or elastin; ameliorating the effects of estrogen imbalance on skin; prevention or amelioration of skin atrophy; prevention and/or reduction in appearance and/or depth of lines and/or wrinkles; prevention, reduction and/or treatment of hyperpigmentation; improvement in skin tone, radiance, clarity and/or tautness; prevention, reduction, and/or amelioration of skin sagging; promotion of anti-oxidant activity; improvement in skin firmness, plumpness, suppleness and/or softness; improvement in procollagen and/or collagen production; improvement in skin texture and/or promotion of retexturization; improvement in skin barrier repair and/or function; improvement in appearance of skin contours; restoration of skin luster and/or brightness; minimization of dermatological signs of fatigue and/or stress; resistance to environmental stress; replenishment of essential nutrient and/or constituents of in the skin decreased by aging and/or menopause; improvement in communication among skin cells; increase in cell proliferation and/or multiplication; increase in skin cell metabolism decreased by aging and/or menopause; retardation of cellular aging; inhibition of enzymes in the skin that accelerate aging of skin cells; minimization of skin dryness and/or improvement in skin moisturization; minimization of skin discoloration; promotion and/or acceleration of cell turnover; enhancement of skin thickness; increase in skin elasticity and/or resiliency; and enhancement of exfoliation.

"Individual In Need": The term "individual in need" means an individual or a specified portion of an individual, e.g., undereye skin, lips, thighs, etc. for which a need is manifest, that stands to benefit from an improved aesthetic appearance of skin or hair by topically treating the individual in need or specified portion of that individual, and more specifically the term further includes an individual that stands to benefit from reducing one of more visible signs of skin damage or aging.

"Lightening Benefit" The term "lightening benefit" means: normalizing, reducing. ameliorating, or reversing a degree of a subject's pigmentation that results from the presence of one or more of the different types of melanin biosynthesized in skin and/or follicles and deposited in hair or skin, relative to a subject's baseline pigmentation.

"Lightening Skin" The term "lightening skin" means eradicating, reducing, ameliorating, and/or reversing a baseline degree of subject pigmentation. Lightening skin may be measured by observing changes in Fitzpatrick scale value of a subject. The Fitzpatrick Scale (aka Fitzpatrick skin typing test or Fitzpatrick phototyping scale) is a numerical classification schema for the color of skin, and remains a recognized tool for dermatologic research into the color of skin. The Fitzpatrick Scale measures several components, including Genetic Disposition, Reaction to Sun Exposure and Tanning Habits.

Type I (scores 0-7) White; very fair; freckles; typical albino skin.
Always burns, never tans
Type II (scores 8-16) White; fair.
Usually burns, tans with difficulty
Type III (scores 17-24) Beige; very common.
Sometimes mild burn, gradually tans to a light brown
Type IV (scores 25-30) Beige with a brown tint; typical Mediterranean Caucasian skin
Rarely burns, tans with ease to a moderate brown.
Type V (scores over 30) Dark brown.
Very rarely burns, tans very easily
Type VI Black.
Never burns, tans very easily, deeply pigmented.

"Modulator" The term "modulator" encompasses any substance, including, without limitation, organic molecules; biomolecules (e.g., peptides, proteins, antibodies, nucleic acid oligomers, etc.); and combinations of substances, such as botanical extracts. The modulators modulate the cellular levels of dyneins, by which is meant that the cellular levels of dynein protein are either increased or decreased by the candidate substance. The term "modulation" may refer to up-regulation, induction, stimulation, potentiation, and/or relief of inhibition, as well as inhibition, attenuation and/or down-regulation or suppression. The modulators may be, without limitation, inhibitors or antagonists, which are, for example, compounds that bind to, partially or totally block stimulation, decrease, prevent, delay activation, inactivate, desensitize, or down-regulate expression levels of genes or dynein proteins or peptides. The modulators may also be, without limitation, activators or agonists, which are compounds that, for example, bind to, stimulate, increase, open, activate, facilitate, enhance activation, sensitize, or up-regulate expression levels of genes or dynein proteins or peptides. The mechanism by which the protein level is modulated is not important.

"Photo-Aging" The term "photo-aging" means the damage that is done to the skin from prolonged exposure, over a person's lifetime, to UV radiation. Most of the skin changes that occur as we get older are accelerated by sun exposure. Examples of skin changes from photoaging include:
  Dark spots
  Wrinkles
  Droopy skin
  A yellowish tint
  Broken blood vessels
  Leathery skin
  Skin cancers "Prevent" or "Preventing" As used herein, the terms "prevent," "preventing," prevention, etc. mean delaying the onset of, hindering the progress of, hindering the appearance of, protection against, inhibiting or eliminating the emergence of, or reducing the incidence of various cosmetic or dermatologic conditions, damages, effects or symptoms. Use of the term "prevention" is not meant to imply that all subjects in a subject population administered the cosmetic composition will always be unaffected by or fail to develop the cosmetic or dermatologic conditions, damage, effect or symptom, but rather that the subject population will exhibit a reduction in the cosmetic or dermatologic damages, effects, or symptoms. For example, many flu vaccines are not 100% effective in preventing the flu in those administered the vaccine.

"Providing A Benefit To Human Skin" Providing a benefit to human skin includes, but is not limited to: (a) treatment of prevention of a sign of skin aging; (b) treatment and/or prevention of fine lines or wrinkles; (c) reduction of skin pore size; (d) improvement in skin thickness, plumpness, and/or tautness; (e) improvement in skin suppleness and/or softness; (f) improvement in skin tone, radiance, and/or clarity; (g) improvement in skin texture and/or promotion of retexturization; (h) improvement in skin barrier repair and/or function; (i) improvement in appearance of skin contours; (j) restoration of skin luster and/or brightness; (k) replenishment of essential nutrients and/or constituents in the skin; (l) improvement of skin appearance decreased by menopause; (m) improvement in skin moisturization and/or hydration; (n) increase in and/or preventing loss of skin elasticity and/or resiliency; (o) improvement in procollagen and/or collagen synthesis; (p) treatment and/or prevention of skin sagging or atrophy; (q) enhancing exfoliation and/or reducing dryness; (r) treatment and/or prevention of skin hyperpigmentation; (s) improvement in skin lightening; (t) treatment and/or prevention of excess sebum output; (u) treatment and/or prevention of cellulite; and (v) improving the aesthetic appearance of skin.

"Sufficient To Decrease Skin Hyperpigmentation" means: eradicating, reducing. ameliorating, or reversing a degree of subject pigmentation that results from increased presence of one or more of the different types of melanin biosynthesized in skin and deposited in skin, relative to a subject's baseline pigmentation.

"Treatment" as used herein, as well as related terms such as "treat" or "treating," refers to eradicating, reducing, ameliorating, or reversing one or more of the unwanted features associated with the skin condition being treated, such that the consumer perceives an improvement or other treatment benefit with respect to the condition.

"Thin Skin" includes skin that becomes thinner with chronological aging, in particular thinning skin in females, especially women 35 years and older, and especially, pre-menopausal and menopausal women, as well as prematurely thinned skin, which may be caused, for example, by photo-aging. In one embodiment, the prematurely thinned skin has been diagnosed as such by a clinician.

As used herein, the term "consisting essentially of" is intended to limit the invention to the specified materials or steps and those that do not materially affect the basic and novel characteristics of the claimed invention, as understood from a reading of this specification. All percentages are by weight based on the total weight of the composition, unless otherwise indicated.

In one embodiment, the benefits and improvements to the aesthetic appearance of skin arising from the use of, i.e., skin treatment with, the candidate substance of the invention is manifest in one or more of the following: reduction in pore size; improvement in skin tone, radiance, clarity and/or tautness; promotion of anti-oxidant activity; improvement in skin firmness, plumpness, suppleness, and/or softness; improvement in skin texture and/or promotion of retexturization; improvement in skin barrier repair and/or function; improvement in appearance of skin contours; restoration of skin luster and/or brightness; improvement in communication among skin cells; increase in cell proliferation and/or multiplication; increase in skin cell metabolism decreased by aging and/or menopause; improvement in skin moisturization; promotion and/or acceleration of cell turnover and enhancement of exfoliation; reducing dermatological signs of chronological aging, photo-aging, hormonal aging, and/or actinic aging; preventing, ameliorating, and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and in one embodiment deep wrinkles or creases; preventing, reducing, and/or diminishing the appearance and/or depth of lines and/or wrinkles; improving the appearance of suborbital lines and/or periorbital lines; improvement in appearance of skin contours, hollow cheeks, sunken eyes, reducing the appearance of crow's feet; rejuvenating and/or revitalizing skin, in one embodiment aging skin; reducing skin fragility; ameliorating the effects of estrogen imbalance; preventing, reducing, and/or reversing skin atrophy; improving skin tone tautness; preventing, reducing, and/or ameliorating skin sagging; preventing, reducing, and/or ameliorating thinning skin; improving skin firmness, plumpness, and/or suppleness; increase in collagen; decrease in collagenase; increase in elastin; decrease in elastase; increase in skin glycosaminoglycan content; and increase in skin hyaluronic acid content, with or without the use of alpha or beta hydroxy acids, keto acids or other exfoliants.

In one embodiment, the anti-aging benefit arising from the use of, i.e., skin treatment with, the candidate substance of the invention is selected from the group consisting of: improvement in communication among skin cells; reduction, amelioration, and/or prevention of fine lines or wrinkles; improvement in procollagen and/or collagen production; improvement in skin texture and/or promotion of retexturization; improvement in skin barrier repair and/or function; amelioration, reduction and/or prevention of skin sagging or atrophy; restoration of skin luster and/or brightness; replenishment of essential nutrients and/or constituents in the skin; improvement of skin appearance decreased by menopause, including thinning skin; improvement in skin moisturization and/or hydration; improving procollagen and/or collagen production; improving skin texture and/or promoting retexturization; improving skin barrier repair and/or function; improving the appearance of skin contours; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; enhancing exfoliation; improving microcirculation; decreasing and/or preventing cellulite formation; decreasing pigmentation; lightening skin; treating hyperpigmented skin; increasing skin thickness; increase in collagen; decrease in collagenase; increase in elastin; decrease in elastase; increase in skin glycosaminoglycan content; increasing skin hyaluronic acid content; and any combinations thereof.

In another embodiment, the improvement in aesthetic appearance by modulating lipid production in the skin by use of, i.e., skin treatment with, the candidate substance of the invention may be any of the following: improvement in skin moisturization; enhancement of skin thickness; reducing skin sensitivity; reduction in appearance of cellulite lumpiness and/or unevenness; reduction in pitting appearance of cellulite upon squeezing; reduction in extent of area affected by cellulite; prevention or delay in recurrence of cellulite; prevention or treatment of acne; decrease in intracellular neutral sebum lipids; decrease in intracellular adipocyte and/or preadipocyte triglycerides; prevention, reduction, or amelioration of oily skin; reduction in subcutaneous fat deposition and/or accumulation; improvement in collagen deposition; and improvement in connective tissue strength.

In another embodiment, the benefits and improvements to the lightening of skin using, i.e., skin treatment with, the candidate substance of the present invention is manifest in one or of the following: decrease in skin melanin content; decrease in skin melanogenesis; diminishing age spots; lightening a suntan; evening, normalizing, or optimizing skin tones, e.g., in areas of mottled hyper-pigmentation; in treating melasmic and chloasmic patches, freckles, afterburn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

In one embodiment, administration of the candidate substance of the present invention results in no significant toxicity to the target cells, as may be measured by a suitable MTT viability assay.

In one embodiment, administration of the candidate substance of the present invention results in modulation of skin pigmentation, as may be measured utilizing a suitable B16 melanoma (melanin content) or A2058 (melanogenic activity) assay.

In one embodiment, administration of the candidate substance of the present invention results in a slowing in collagenase-mediated collagen breakdown, as may be measured utilizing a suitable gelatin zymography assay.

In one embodiment, administration of the candidate substance of the present invention results in prevention of extracellular matrix breakdown by increase or maintenance of glycosaminoglycan synthesis/stability, as may be measured by a suitable GAG synthesis assay.

In one embodiment, administration of the candidate substance of the present invention results in an inhibition of MPP activity and/or decrease of MMP expression.

In one embodiment, administration of the candidate substance of the present invention results in maintenance of and/or improvement of skin strength and elasticity, as may be measured by a suitable collagen synthesis assay.

In one embodiment, administration of the candidate substance of the present invention results in collagen synthesis, repair and/or hydration by increase or maintenance of hyaluronic acid synthesis/stability, as may be measured by a suitable HA synthesis assay.

In one embodiment, administration of the candidate substance of the present invention results in a decrease in lipid production, as may be measured utilizing a suitable intracellular adipocyte triglyceride assay.

In one embodiment, administration of the candidate substance of the present invention results in a decrease in neutral intracellular sebum lipid production, as may be measured utilizing a suitable assay.

In one embodiment, the candidate substance is an extract of *Abutilon indicum*. *Abutilon indicum* (Indian Abutilon, Indian Mallow; is a small shrub in the Malvaceae family, native to tropic and subtropical regions and sometimes cultivated as an ornamental. This plant is used as a medicinal plant and is considered invasive on certain tropical islands. *Abutilon* is a large genus of about 150 species of broadleaf evergreens in the mallow family (Malvaceae). The genus includes annuals, perennials, shrubs, and small trees from 1-10 m tall, and is found in the tropical and subtropical regions of all continents. The leaves are alternate, unlobed or palmately lobed with 3-7 lobes. The flowers are conspicuous, with five petals, mostly red, pink, orange, yellow or white. Branched, half-woody, erect shrub, growing up to 2 meters high. Leaves are green and toothed, orbicular-ovate to broadly ovate, 5-12 cm long and nearly as wide, with a prominently heart shaped base and pointed apex, the margins entire or irregularly toothed. Flowers are yellow, solitary, and opens in the evening. Fruits are rounded capsules, 1.5 to 2 cm in diameter, with 15-20 hairy, awned carpels. *Abutilon indicum* is used as an expectorant, cholagogue, as an antiseptic in urinary tract infection and as a drug stimulating intestinal secretion. An infusion of the root is prescribed in fevers as a cooling medicine, and is considered useful in strangury and hematuria. Plant leaves are demulcent; given as decoction for bronchitis, bilious diarrhea, gonorrhea, bladder inflammation, urethritis and fevers. Bark is astringent and diuretic. Seeds are demulcent, laxative, expectorant and aphrodisiac; useful for gonorrhea and cystitis.

In one embodiment, the extract of the present invention is derived using water and ethanol extraction. In another embodiment, the extract is derived from the entirety of the plant.

The extract of the above-noted plants may be obtained by distilling the raw materials with a stripping agent. The stripping agent may be a liquid that is miscible, immiscible, or partially miscible with the desired extract from the plants. Suitable stripping agents include, but are not limited to, water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); dimethyl sulfoxide; acetonitrile; other organic solvents; and combinations thereof. In one embodiment, the stripping agent is immiscible with the desired extract (e.g., essential oil) from the plant. In one embodiment, the stripping agent is water. In one embodiment, the extract is obtained by steam distillation. The extract (e.g., essential oil) may be collected by phase separation from the stripping agent. It is believed that the stripping agent increases the overall vapor pressure of a distillation system for obtaining an extract and thereby reducing the boiling point of the desired product, the extract.

In other embodiments, the botanical component may be in the form of an extract obtained by solvent extraction. In one embodiment the botanical material is obtained by organic solvent extraction(s). Briefly, the organic solvent extraction method involves washing and extracting the raw materials, which may be whole or ground into small particle sizes, using an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field. The raw materials are pushed in the extracting machine by a thruster, which slowly moves the plant raw materials forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time suitable to extract the plant constituents is used, typically between about 1-10 hours is suitable, in one embodiment is between about 2-8 hours, in one embodiment is between about 3-6 hours. The temperature of extraction is between about 30° C.-100° C., in one embodiment between about 40° C.-70° C., and in one embodiment between about 50° C.-60° C. The collected extract is then fine-filtered to remove debris, and may be used directly, or is concentrated, for example by distilling the solvent or by other conventional processing. The solution of extract actives may be rotary evaporated under vacuum or lyophilized. A typical extract's actives content is above about 25%, in one embodiment above 50%, and the extract can also be provided an essential oil or a concentrate having a semi-solid or solid consistency.

Similarly, aqueous-organic solvent extraction involves initially collecting raw materials from the plants, which may be whole or ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above. The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. Alternatively, organic solvent may then be added to the neutralized solution to transfer the extract from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly as an essential oil or a concentrate, or dried by a number of different means, such as, for example, air-dried, oven-dried, rotary evaporated under vacuum or lyophilized to a semi-solid or solid consistency.

In one embodiment, the efficacy of the extract of the present invention may be optimized by adjusting the relative presence of various extract fractions present in the extract by, for example, altering the identity and/or relative proportions of the solvents used in the extraction process. In another embodiment, the temperatures and /or other conditions utilized in solvent extraction may be optimized so as to yield an effective extract.

Examples of extraction of extracts of *Abutilon indicum* may be provided below and/or in the incorporations by reference described above.

In another embodiment, extract as used herein, also includes "synthetic" extracts, i.e., various combinations of known plant components and/or constituents that are combined to substantially mimic the composition and/or activity of any one or more of the above-noted plant extracts of natural origin having modulating activities. In one embodiment, the synthetic extracts have substantially the same number of active components as the natural plant material. The correspondence of the numerical incidence of actives between the synthetic extracts and the natural plant material may also be described in terms of "percent commonality." The synthetic extract has about 50 percent or more commonality to the chemical composition of a plant or natural extract. In other words, the synthetic extract has about 50 percent or more of the active ingredients found in the plant or a natural extract. More In one embodiment, the chemical composition of the synthetic extract has about 70 percent or more commonality to the chemical composition of a plant or a natural extract. Optimally, a synthetic extract has about 90 percent or more commonality to the chemical composition of a plant or a natural extract.

The cosmetic compositions according to the invention can be formulated in a variety of forms for topical application and will comprise from about 0.00001% to about 90% by weight of one or more candidate substances, in one embodiment comprising such actives in an amount from about 0.001% to about 25% by weight, in another embodiment from about 0.01% to about 2% by weight, and in another embodiment from about 0.1% to about 1% by weight.

The compositions according to the invention can be formulated in a variety of forms for topical application and will comprise from about 0.0001% to about 90% by weight of an extract of extracts of *Abutilon indicum*, and preferably will comprise from about 0.001% to about 25% by weight, and more preferably from about 0.01% to about 10% by weight. Within the more preferred range, the composition may comprise an *Abutilon indicum*, extract within a range from about 0.1%, 0.25%, 0.5%, 0.75% or 1% up to 5%, 7.5% or 10% by weight of the total composition.

Another embodiment of the invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, in one embodiment as a lotion or cream, but also in an anhydrous or aqueous base, as well as in a sprayable liquid form. Suitable cosmetic product forms for the compositions of this invention include, for example, an emulsion, a cream, a balm, a gloss, a lotion, a mask, a serum, a toner, an ointment, a mousse, a patch, a pomade, a solution, a spray, a wax-based stick, or a towelette. In addition, the compositions contemplated by this invention can include one or more compatible cosmetically acceptable adjuvants commonly used and known by the skilled practitioner, such as colorants, fragrances, film formers, pH adjusting agents, humectants, preservatives, solvents, emulsifiers and other surface active agents, gelling agents, rheology modifiers, fillers and bulking agents, stabilizers, chelating agents, pH adjusting agents, thickeners, waxes, and the like, and as further described below.

Also, embraced by the invention are transdermal modes of delivery, such as patches and the like, with or without suitable penetration enhancers. The methods and compositions embodied by the invention provide a means by which the modulators can be effectively administered in a transdermal system. Accordingly, a transdermal means of delivering a composition or formulation (often with a penetration enhancing composition) to the skin is that of the transdermal patch or a similar device as known and described in the art. Transdermal patches are designed to deliver an effective amount of compound across a user's skin. Transdermal patches typically involve a liquid, gel, solid matrix, or pressure-sensitive adhesive carrier into which the modulator may be incorporated. Patch formulations and preparation are well known in the art. See for example "Dermatological and Transdermal Formulations" (Drugs and the Pharmaceutical Sciences, Vol 119) by Kenneth A Walters (Editor), Marcel Dekker and "Transdermal Drug Delivery" (Drugs & the Pharmaceutical Sciences) by Richard H. Guy (Editor), Jonathan Hadgraft (Editor) 2nd Rev& ex edition Marcel Dekker and "Mechanisms of Transdermal Drug Delivery" (Drugs & the Pharmaceutical Sciences, Vol 83) edited by Russell O. Potts and Richard H. Guy (1997). Examples of such devices are disclosed in U.S. Pat. Nos. 5,223,262; 4,820,724; 4,379,454; and 4,956,171; and U.S. Patent Publication No. US20110300198, all of which are incorporated herein by reference and such descriptions are not meant to be limiting. The transdermal mode of storing and delivering the compositions onto the skin, including hair, and forming the active composition is convenient and well-suited for the purposes of an embodiment of the present invention. In a preferred method, the application is through a sustained release vehicle, carrier, or diluent, e.g., a topically applied sustained released patch. In one embodiment, when a topical patch is used, the patch is applied to the desired area for extended period of time. In one embodiment, the extended period of time is greater than one hour, in one embodiment the extended period of time is overnight, i.e., when the user is sleeping. In a further embodiment of the current invention, the transdermal patch may be applied to skin exhibiting impaired cytoskeleton and/or nuclear envelope integrity, loss of proper cell polarity and/or alignment, and disregulation of wound healing and/or skin regeneration, which may lead to lines/wrinkles, sagging, and other signs of aging and/or photoaging or at risk for exhibiting impaired cytoskeleton and/or nuclear envelope integrity, loss of proper cell polarity and/or alignment, and disregulation of wound healing and/or skin regeneration, which may lead to lines/wrinkles, sagging, and other signs of aging and/or photoaging, i.e., the buttocks, thighs, hips, or limbs for extended periods of time, at least one day, two or more days, at least a week, or longer if necessary in order to provide prolonged exposure to the −2 modulators in order to achieve the desired enhancements of the skin in need of treatment.

The vehicle may comprise an aqueous phase, an oil phase, an alcohol, a silicone phase or any combination thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion preferably has one or more lipophilic organic compounds, including emollients; humectants (such as butylene glycol, propylene glycol, Methyl gluceth-20, and glycerin); and/or other oil-dispersible or oil-soluble components. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a single oil or mixtures of different oils. The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A are also contemplated to be suitable. Various commercially available $C_{16}$ isoparaffins, such as isohexadecane (having the tradename Permethyl) are also suitable. Examples of preferred volatile hydrocarbons include polydecanes such as isododecane and isodecane, including for example, Permethyl-99A (Presperse Inc.) and the $C_{7-8}$ through $C_{12-15}$ isoparaffins such as the Isopar Series available from Exxon Chemicals. A representative hydrocarbon solvent is isododecane.

Non-limiting emulsifiers include nonionic, anionic, amphoteric, and zwitterionic surface active agents. In one embodiment the emulsifiers are nonionic surface active agents. Suitable emulsifiers include but are not limited to emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. The preferred emulsifiers include soya sterol, cetyl alcohol, stearic acid, emulsifying wax, acrylates, silicone containing emulsifiers and mixtures thereof. Other specific emulsifiers that can be used in the composition of the present invention include, but are not limited to, one or more of the following: $C_{10-30}$ alkyl acrylate crosspolymer; Dimethicone PEG-7 isostearate, acrylamide copolymer; sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 13th Edition 2010, the disclosure of which is hereby incorporated by reference. These emulsifiers typically will be present in the composition in an amount from about 0.001% to about 10% by weight, in particular in an amount from about 0.01% to about 5% by weight, and more preferably, from about 0.1% to about 3% by weight.

The oil phase may comprise one or more volatile and/or non-volatile silicone oils. The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water. Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200 Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted with various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)$_m$- and/or —(PO)$_n$ groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

The water-in-silicone emulsifiers typically will be present in the composition in an amount from about 0.001% to about 10% by weight, in particular in an amount from about 0.01% to about 5% by weight, and more preferably, below 1% by weight. The aqueous phase of the emulsion may include one or more additional solvents, including lower alcohols, such as ethanol, isopropanol, and the like. The volatile solvent may also be a cosmetically acceptable ester such as butyl acetate; or the like.

The compositions may include liposomes. The liposomes may comprise other additives or substances and/or may be modified to more specifically reach or remain at a site following administration.

The composition may optionally comprise other cosmetic actives and excipients, obvious to those skilled in the art including, but not limited to, antioxidants, emollients, humectants, moisturizers, vitamins, minerals, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, $H_1$ or $H_2$ antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants such as Vaseline, depigmenting agents, hypopigmenting agents, preservatives (e.g., DMDM Hydantoin/Iodopropynylbutylcarbonate), pharmaceutical agents, photostabilizing agents, and compatible mixtures thereof. In addition to the foregoing, the cosmetic compositions of the invention may contain any other compound for the treatment of skin disorders.

Various fillers and additional components may be added. Fillers are normally present in an amount of about 0 weight % to about 20 weight %, based on the total weight of the composition, in one embodiment about 0.1 weight % to about 10 weight %. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

Colorants may include, for example, organic and inorganic pigments and pearlescent agents. Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment.

In one embodiment of the invention, the compositions may include additional skin actives such as, but not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, and advanced glycation end-product (AGE) inhibitors.

In a specific embodiment, the composition may comprise at least one additional botanical, such as, for example, a botanical extract, an essential oil, or the plant itself. Suitable botanicals include, without limitation, extracts from *Abies pindrow, Acacia catechu, Anogeissus latifolia, Asmunda japonica, Azadirachta indica, Butea frondosa, Butea monosperma, Cedrus deodara, Emblica officinalis, Ficus benghalensis, Glycyrrhiza glabra, Ilex purpurea Hassk, Inula racemosa, Ligusticum chuangxiong, Ligusticum lucidum, Mallotus philippinensis, Mimusops elengi, Morinda citrifolia, Moringa oleifera, Naringi crenulata, Nerium indicum, Psoralea corylifolia, Stenoloma chusana, Terminalia bellerica*, tomato glycolipid and mixtures thereof.

The composition may comprise additional active ingredients having anti-aging benefits, as it is contemplated that synergistic improvements may be obtained with such combinations. Exemplary anti-aging components include, without limitation, botanicals (e.g., Butea frondosa extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates); exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, cetyl ethylhexanoate, C12-15 alkyl benzoate, isopropyl isostearate, diisopropyl dimer dillinoeate, or any mixtures thereof. The emollient may be, in one embodiment, present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. Preferred sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alphahydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

Barrier enhancers include ceramides, essential fatty acids and their esters, especially glycerides, α-hydroxy fatty acids and their esters derived with alkanols through carboxylic hydroxyl or with other fatty acids at the omega-hydroxyl, the latter type being most preferred, with phospholipids, cholesterol and its esters, such as cholesteryl hemisuccinate and cholesteryl phosphate of which cholesterol phosphate and essential fatty acids are most preferred, cholestanol and its derivatives. This agent can be added to a topical composition either as singular molecular entities or as a complex mixture of lipids derived from either synthetic, animal or plant sources.

Antioxidants scavenge free radicals from skin, protecting the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant, in one embodiment from about 0.001 wt % to about 10 wt %, and in one embodiment from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

In one embodiment, the composition of the invention may have a pH between about 1 and about 8.5. In certain embodiments, the pH of the composition will be acidic, i.e., less than 7.0, and in one embodiment will be between about 2 and about 7, in one embodiment between about 3.5 and about 5.5.

In one embodiment, the composition is intended for use as a non-therapeutic treatment. In another embodiment, the composition is an article intended to be rubbed, poured, sprinkled, or sprayed on, introduced into, or otherwise applied topically to the human body for cleansing, beautifying, promoting attractiveness, or altering the appearance, in accordance with the US FD&C Act, sec. 201(i).

In another embodiment, the compounds or agents are intended for oral use, including for pharmaceutical use. Pharmaceutical formulations will include pharmaceutically acceptable carriers (i.e., diluents and excipients). The pharmaceutical compositions may be included in solid dosage forms, including compressed tablets and capsules, or in liquid or powder forms. Pharmaceutical dosage forms will typically include from about 0.5 mg to about 200 mg, or from about 1 mg to about 100 mg of the modulator. The dosage forms may be immediate release, in which case they will typically comprise a water-soluble or dispersible carrier such as microcrystalline cellulose, mannitol, hydroxypropyl methyl cellulose, PVP or the like, or may be delayed, sustained, or modified release, in which case they may comprise water-insoluble polymers such as cellulose ethers (e.g., ethylcellulose), alone or in combination with water soluble or dispersible polymers The invention also provides a non-therapeutic method for treating aging skin; hyperpigmented skin; skin in need of aesthetic improvement; skin affected by cellulite; and/or wrinkled skin by topically applying a composition comprising the inventive composition over the affected area for a period of time sufficient to reduce, ameliorate, dermatological signs of aging, hyperpigmentation, aesthetic decline, cellulite, and/or wrinkles. The composition will typically be applied, e.g., as a thin film, to the skin 1, 2, or 3 times per 24 hours for as long as is necessary to achieve desired results. The treatment regiment may comprise daily application for at least one week, at least two weeks, at least four weeks, at least eight weeks, or at least twelve weeks. The method includes treatment of skin changes associated with both chronological and intrinsic skin aging.

The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the composition of the invention will be applied to the skin in an amount from about 0.001 to about 100 mg/cm$^2$, typically from about 0.01 to about 20 mg/cm$^2$, and more typically about 0.1 to about 10 mg/cm$^2$.

In a specific embodiment, the extracts of *Abutilon indicum* are provided in a physiologically, cosmetically, and dermatologically-acceptable vehicle, diluent, or carrier, where the composition is topically applied to an affected area of skin and left to remain on the affected area in an amount effective for improving the condition and aesthetic appearance of skin.

The method of the invention may be employed prophylactically to forestall aging including in patients that have not manifested signs of skin aging, most commonly in individuals under 25 years of age. The method may also reverse or treat signs of aging once manifested as is common in patients over 25 years of age.

Sample Formulations

Exemplary cosmetic compositions comprising extracts of *Abutilon indicum* for topical application to skin exhibiting or at risk of exhibiting which may lead to cellulite are provided in Table 1.

TABLE 1

Sample Cosmetic Composition

*Abutilon indicum* extract
Aesthetic modifier
Emollient
Emulsifier
Anti-inflammation agent
Chelater
Coolant
Elastin stimulator
Exfoliator
Fragrance
Humectant
Microcirculation enhancer
Neutralizer
Preservative
Sunscreen
Collagenase/elastinase inhibitor
Hawthorne (*Crataeg. Monog.*) Fruit. Extract
Coffee Seed Extract
Soybean (*Glycine soja*) Extract
*Celosia cristata* Extract & *Prunella vulgaris* Extract
L-Carnitine Hydrochloride
*Averrhoa carambola* Leaf Extract
Demineralized water B. Exemplary Anti-Aging Facial Cosmetic Composition Exemplary cosmetic compositions comprising extracts of *Abutilon indicum* for topical application to areas of the face exhibiting or at risk of exhibiting signs of aging are provided in Table 2.

TABLE 2

Sample Anti-aging Facial Cosmetic Composition

*Abutilon indicum* extract
Aesthetic modifier
Emollient
Emulsifier
Anti-inflammation agent
Chelater
Coolant
Elastin stimulator
Exfoliator
Fragrance
Humectant
Microcirculation enhancer
Neutralizer
Preservative
Sunscreen
Collagenase/elastinase inhibitor
Phytol
Antioxidant
Fennel Extract
Carrot extract
Pomegranate extract
Thiodipropionic acid (TDPA)
Green tea polyphenol
L-4 Thiazolylanine
Demineralized water Exemplary Skin Lightening Compositions Exemplary cosmetic compositions comprising an extract of *Abutilon indicum* for topical application to skin exhibiting signs of hyperpigmentation.

TABLE 3

Sample Skin Lightening Compositions Description

Demineralized Water
Carbopol 934
Acrylates/C10-30 Alkyl Acrylate Crosspolymer

TABLE 3-continued

Sample Skin Lightening Compositions Description

Acrylates/C10-30 Alkyl Acrylate Crosspolymer
Xanthan Gum
Disodium EDTA - Tech Grade
Methylparaben
Alcohol SD40B
Alcohol Mixture (3210&1901 92.52-7.48)
Alcohol Mixture (3215&1901 92.52-7.48)
Phenoxyethanol-98% MIN (*RI*)
Butylene Glycol
Pentylene Glycol (*RI*)
Ethoxydiglycol
ISODODECANE
Dilauryl Thiodipropionate
Tetrahexyldecyl Ascorbate
Ascorbyl Glucoside
Glycyrrhizinate - Dipotassium Unp.
Silica Shells
Sodium Hydroxide Solution 50%
Silicone Fluid SF-96-5
PEG-40 Stearate
Steareth-2
*Saxifraga Sarmentosa*/Grape Extract
*Saccharomyces*/Zinc ferment
Yeast Extract
Kudzu (*Pueraria Lobata*) Symbiosome extract
Soybean (*Gly. Soja*) Extract
Carrot (*Daucus Carota Sativa*) Root Extract
Phytol
Dimethicone/Dimethicone Crosspolymer
Thiodipropionic Acid
*Abutilon indicum* extract The following examples describe specific aspects of the invention to illustrate the invention but should not be construed as limiting the invention, as the examples merely provide specific methodology useful in the understanding and practice of the invention and its various aspects. Unless otherwise indicated, control values were obtained using samples having added medium in place of various concentrations of candidate substances.

EXAMPLE 1

Preparation of Candidate Substance

EXAMPLE 1A

Butanolic/Water Extract

*Abutilon indicum* whole plant components were gathered and then chopped. The chopped flower components were then ground and a 50% ethanol solution was added to the chopped flower components. The solution was filtered and the filtrate vacuum evaporated to yield a concentrated extract of approximately 600 ml, which was then diluted with pure water. The diluted extract was vacuum evaporated, then again diluted with pure water. The diluted extract was left to stand at 4 C for 12 hours, then centrifuged and filtered. 3× extraction with hexane followed this filtration step, with the hexane layer and aqueous layers subsequently being separated. Charcoal was added to the aqueous layer and the charcoal/extract mixture was then centrifuged and filtered. The filtered extract was then extracted 3× with water-saturated n-butanol, with the butanolic (upper) and aqueous layers subsequently separated. The butanolic layer was pooled, rotary evaporated, and lyophilized, yielding a first butanolic extract. The aqueous layer was concentrated (with foam or precipitate, if any) by rotary evaporator under vacuum, lyophilized, and yielded a second aqueous extract. Unless otherwise noted below, all experiments except the in vivo assay (Example 14) described below utilized the butanolic/water extract described above, in particular utilizing the second aqueous extract described herein.

EXAMPLE 1B

Ethanol/Water Extract

*Abutilon indicum* leaf components were gathered and then dried. The dried aerial components were then ground and added to a 50%/50% water/ethanol solution. The components/water/ethanol slurry was then subjected to solid/liquid separation; the resultant cake was discarded and the solvent was concentrated and desolvented to yield a soft extract. The soft extract was then spray-dried after mixing with maltodextrin; sieved; and stored in dry state for later reconstitution. This ethanol/water extract was utilized in the in vivo biopsy (Example 14) below.

As noted in the remaining specification, modifications and adaptations of the above-noted extraction process are possible, particularly during a scale-up to larger volumes for production.

EXAMPLE 2

HPLC of Candidate Substance

Extracts were generally characterized by high performance liquid chromatography. A sample size of approximately 5 mg/mL was dispersed in 25/75 MeOH/H$_2$O and sonicated. The characterization was performed on a Zorbax SBC-18 column (7.5 cm×4.6 mm, 3.5 um particle size) and detection was achieved using diode array UV absorbance, 260 nm 300 nm and 360 nm, with lines on FIG. 1 depicted in ascending order and 260 nm on bottom. Operating conditions were flow rate 1.5 ml/min; temperature, 40° C.; sample injection volume, 20 µL, and time of run, 19 minutes. The mobile phase gradient used was as follows. In one embodiment, the butanol/water extracted composition of a b compound, in substantial isolation, exhibits an HPLC profile substantially similar to that depicted herein in FIG. 1.

EXAMPLE 3

MTT Growth Assay

Fibroblast (2.0×10$^3$ cells/well), A2058 human melanoma cells and B16F10 mouse melanoma cells (1.0×10$^3$ cells/well) were plated in 96 well plates in 100 µL medium, and incubated before sample treatment at 37° C. for 24 hours. After 24 hours, various concentrations of candidate substances were added in medium (100 µL) and incubated for another 48 hours. The metabolic activity of each well was determined by the MTT assay and related to untreated cells. After removal of 100 µL medium, MTT stock dye solution was added (15 µL/100 µL medium) to each well, the plate was incubated at 37° C. in 5% CO$_2$ atmosphere. After 4 hours, 100 µL of the solubilization/stop solution was added to each well and mixed thoroughly to dissolve the dye crystals. The absorbance was measured by using ELISA plate reader at 540 nm with a reference wavelength of 630 nm, and the extract of the present invention had no adverse effect on cell growth as assessed using this protocol.

EXAMPLE 4

B16 Melanin Content Assay

Melanin content assay was measured by assaying the soluble melanin extracted from B16F10 lines afterexposure to plant extracts. Briefly, B16F10 mouse melanoma cells were seeded into culture dishes at a density of 2.5×10$^5$ and cultured for 48 h. The medium was replaced with fresh medium containing various concentrations of plant extracts. The B16F10 were incubated for 48 hr. Then the cells were harvested and washed with ice-cold PBS (pH 7.4) 2 times. Melanin contents were measured by UV-visible spectrophotometer at 405 nm. Relative to B16F10 mouse melanoma cells treated with control (media), B16F10 mouse melanoma cells treated with a *Abutilon indicum* candidate extractexhibited approximately 57% of the melanin content of cells incubated with control media (when *Abutilon indicum* candidate extract was at a final concentration of 50 ug/ml in the media).

EXAMPLE 5

Melanogenic Assay

Melanogenic activity was measured by measuring the radioactive melanin formed as $^{14}$C-DOPA is converted to the acid insoluble melanin biopolymer in A2058 human melanoma cells and/or in mouse B16F10 melanoma cells. Cells were seeded into a 6 well-plate at a density of 1.0×10$^5$ cell/well and cultured for 24 h. The media were then replaced with fresh experimental media containing plant extracts and 0.1 µCi of $^{14}$C-DOPA (Amersham Pharmacia Biotect). The cells were optionally exposed briefly to UV light, then further incubated for 48 h in media containing candidate substances. After incubation, media were discarded and the cells were rinsed with PBS, lysed by adding 200 µL of 1.5 N NaOH and incubating at 37° C. for 30 min, and then neutralized with 100 µL of 3 N HCl. The resulting cell lysates were transferred into liquid scintillation vials and mixed with scintillation cocktail, and the radioactivity was determined by Beckman scintillation counter. A portion of cell lysate was kept and the protein content was determined by Bradford method. The $^{14}$C-DOPA incorporation into melanin was expressed as CPM/mg protein. Relative to A2058 cells treated with control (media), A2058 cells treated with a *Abutilon indicum* candidate substance synthesized approximately 82% (no UV)/93% (UV) of melanin (when *Abutilon indicum* was at a final concentration of 50 ug/ml in the media). B16 cells under otherwise identical conditions (no UV) synthesized approximately 69% of melanin compared to cells incubated with control media.

EXAMPLE 6

MMP-2 Gel Zymography Assay

Normal human fibroblast cells were cultured in T25 cm$^3$—flask. Confluent cells were treated for 48 h with DMEM without phenol-red growth medium. The fibroblast supernatants were subjected to substrate gel electrophoresis in 10% polyacrylamide gels impregnated with 1 mg/ml gelatin. Samples of cell supernatants (0.5 microgram of protein) were mixed with an equal volume of non-reducing Laemmli sample buffer (2% SDS; 125 mM Tris-HCl, pH 6.8, 10% glycerol and 0.001% bromophenol blue) and then electrophoresed. After electrophoresis gels were washed twice in 2% Triton X-100 for 60 min at room temperature and then incubated at 37° C. for 16 h in 50 mM Tris-HCl buffer, pH 7.4 containing 5 mM $CaCl_2$. Following incubation, the gels were stained with 0.05% Coomassie Brilliant Blue G-250. Gelatinolytic activity was detected as unstained bands. The relative molecular masses of proteases will be determined by the relation of log Mr to the relative mobility of Sigma SDS-PAGE molecular weight markers. In order to examine the effect of plant fractions on enzyme activity, conditioned medium containing MMPs was loaded on preparative gelatin-containing polyacrylamide gels. After electrophoresis the gels were cut in strips of 1 cm, and each strip was incubated at 37° C. for 16 h in Tris-$CaCl_2$ buffer containing various concentrations of plant fractions. The gels were then extensively washed in 2% Triton X-100 and reincubated in Tris-$CaCl_2$ solution for 16 h at 37° C. In order to quantify the relative inhibition of MMPs by plant fractions, electrophoretic bands were scanned and analyzed by comparing the activity of MMPs with control reactions, where the plant fractions were not included. Relative to human fibroblast cells treated with control (media), MMPs in human fibroblast cells treated with a *Abutilon indicum* extractexhibited approximately 37% of the activity of MMPs in human fibroblast cells incubated with control media (when *Abutilon indicum* extractwas at a final concentration of 200 ug/ml in the media).

EXAMPLE 7

Fluorometric Analysis of Collagenase Activity

Putative collagenase inhibiting substances (candidate substances) were diluted in 1× reaction buffer. Add 80 µl volumes of various concentration of candidate substances (or media in the case of controls) were used for each 200 µl reaction. 20 µl of DQ gelatin stock solution (collagen) was added to each assay well giving a DQ final concentration of 12.5 µg/ml. Clostridium collagenase type III enzyme was diluted in 1× Reaction buffer to 0.3 units/ml. 100 µl of the diluted enzyme, or 100 µl of 1× Reaction buffer as a blank, was added to the sample wells preloaded with substrate and inhibitor. The samples were then incubated at 37° C., protected from light, for an appropriate time, e.g. 1-30 mins. Because the reaction is continuous (not terminated), fluorescence was measured at every 1.5 mins. viaspectrofluorometer. Digested products from the DQ gelatin substrates have absorption maxima at 485 nm and fluorescence emission maxima at 528 nm. For each time point, background fluorescence was corrected for by substrating the values derived from the no-enzyme control. Relative to sample wells containing control media (no candidate substances), collagenase activity was approximately 102% of control when using a media with a 200 ug/ml concentration of candidate substance.

EXAMPLE 8

Collagen Assay

Fibroblast cells were seeded in 6-well tissue culture plates at densities of 200,000 cells/well, and grown to 80-90% confluence in Dulbecco's modified Eagle's medium (DMEM) buffered to pH 7.4 and supplemented with 20% heat-inactivated fetal bovine serum. The atmosphere was humidified and maintained at 37° C. in 5% carbon dioxide and 95% air.

Dermal fibroblasts were incubated under nonproliferating conditions in DMEM supplemented with 0.5% dialyzed bovine serum in the presence or absence of candidate substances for 72 h, and 6 h prior to harvest 10 µCi of $(2,3,5-^3H)$-proline was added per well. The medium was changed daily. After 72 h incubation, collagen and noncollagen synthesis were determined as follows:

At the indicated time, medium and cells were collected, frozon at −20° C. and thawed at 37° C. This freezing-thawing process was performed for 3 times. and then precipitated with 25% TCA, centrifuge at 10,000 g for 3 min. The protein precipitate was washed 1× with 10% TCA, 1× with 5% TCA. The acid precipitate was dissolved in 500 µl PBS, pH 7.4. Aliquots of these samples were mixed with 100 pg of albumin and 10 mM $CaCl_2$ and digested at 37° C. for 6 h with 10 units bacterial collagenase III. The collagenase-resistant proteins were precipitated with 25% TCA. After centrifugation at 10,000 g for 3 min, an aliquot of the supernatant (collagenase sensitive protein) was combined with scintillant and counted in a Beckman scintilation counter, along with an aliquot of collagenase-resistant protein. Collagen and noncollagen protein production was determined from $^3$H-proline incorporation (dpm) in collagenase-sensitive and -resistant protein. Relative to dermal fibroblast cells treated with control (media), collagen content of dermal fibroblast cells treated with a *Abutilon indicum* candidate substance was approximately 128% of the collagen content of dermal fibroblasts treated with control media when *Abutilon indicum* candidate substance was at a final concentration of 50 ug/ml in the media).

EXAMPLE 9

GAG Synthesis Assay

Fibroblast cells were seeded in 24-wells tissue culture plates at densities of 50,000 cells/well, and incubated for 24 h in Dulbecco's modified Eagle's medium (DMEM) buffered to pH 7.4 and supplemented with 10% heat-inactivated fetal bovine serum. The atmosphere was humidified and maintained at 37° C. in 5% carbon dioxide and 95% air. Dermal fibroblasts were incubated under nonproliferating conditions in DMEM supplemented with 0.5% dialyzed bovine serum for 24 h and then the fibroblast cells were further incubated under nonproliferating conditions in DMEM supplemented with 0.5% dialyzed bovine serum in the presence or absence of tested compound for 48 h. At the indicated time, the medium was collected for determination of the amount of hyaluronic acid by EL ISA. The 96-well plate was coated with dl-polylysine (100 µg/ml in PBS 7.4) for overnight at 37 ° C. and the plate was washed twice with 1.5 M Sodium chloride. 100 µl of 1% BSA in Sodium phosphate buffer, pH 8.0 was added and incubated at 37° C. for 1 h for block non-specific binding. After incubation, the plate was washed three times with 0.1% BSA-0.05% tween-PBS ,pH 4.8 and then the plate was coated with 0.1 mg/ml hyaluronic acid (Grade IV)(0.123 mg/ml EDAC in borate buffer, pH 5.2) at 37° C. for 1 h. The plate was then washed three times with 0.1% BSA-0.05% tween-PBS. Then the mixture of Biotin-HABP (1: 2,000) and medium of fibroblast culture were added to the plate at 37° C. for 1 h. After incubation the plate was washed four times with BSA-tween-PBS and incubated with 100 µl of streptravidin-HRP at 37° C. for 1 h. At the indicated time, the plate was washed and then incubated with 100 µl of SureBlue™ TMB microwell peroxidase substrate for 5-15 min. The plate was read in a microplate reader at 630 nm. Data were compared with HA standard curve (0-2000 ug/ml). Relative to fibroblast cells treated with control (media), HA content of fibroblast cells treated with a *Abutilon indicum* candidate substance was approximately 241% of the GAG content of dermal fibroblasts treated with control media when *Abutilon indicum* candidate substance was at a final concentration of 50 ug/ml in the media; and 435% of the GAG content of dermal fibroblasts treated with control media when *Abutilon indicum* candidate substance was at a final concentration of 200 ug/ml in the media.

EXAMPLE 10

Modulation of Intracellular Triglycerides

Cryopreserved human primary pre-adipocytes may be harvested from the subcutaneous adipose tissue of a healthy female are obtained from Zen-Bio (Research Triangle Park, N.C.). Following the manufacturer's instructions, the pre-adipocytes are cultured in Preadipocyte Medium containing DMEM/Ham's F-12 (1:1, v/v), HEPES (pH 7.4), fetal bovine serum, penicillin, streptomycin, and amphotericin B (Zen-Bio), in a humidified 37° C. incubator with 5% $CO_2$. After reaching 90% confluence, the pre-adipocytes are induced to differentiate into adipocytes by adding tested active or positive control (PPAR gamma agonist) into Adipocyte Initition Medium containing DMEM/Ham's F -12 (1:1, v/v), HEPES pH 7.4, fetal bovine serum, biotin, pantothenate, human insulin, dexamethasone, isobutylmethylxanthine, penicillin, streptomycin, and amphotericin B (Zen-Bio). After 7 days of incubation, medium is replaced with Maintenance Medium, DMEM /Ham's F -12 (1:1, v/v), HEPES pH 7.4, fetal bovine serum, biotin pantothenate, human insulin, dexamethasone, penicillin, streptomycin, and amphotericin B, and the adipocytes are incubated for another 7 days. The production of triglycerides in the adipocytes is determined by using a triglyceride assay kit (Zen-Bio). Briefly, adipocytes are rinsed with a wash buffer and lysed in a lysis buffer following medium removal. Intracellular triglycerides are released into the lysis buffer and converted into glycerol-1-phosphate, which is subsequently oxidized to di-hydroxyacetone phosphate and hydrogen peroxide. Hydrogen peroxide is reacted with 4-aminoantipyrine (4-AAP) and sodium N-ethyl-N-(3-sulfopropyl)-m-anisidine (ESPA) to generate a quinoneimine dye, which shows an absorbance maximum at 540 nm. The increase in absorbance at 540 nm is directly proportional to the intracellular levels of triglycerides in the adipocytes. Results are obtained in triplicate and a p-value is determined. It is expected that use of an *Abutilon indicum* extract at varying concentration will yield decreased concentration of intracellular trigylcerides in the treated cells.

EXAMPLE 11

Modulation of Intracellular Neutral Sebum Lipids

Human sebocyte cells (SZ95) are plated into 96-well plate (0.125×10⁵ cells/well) containing Sebomed medium (Biochrom, Germany) (DMEM/Ham's F-12 (1:1, v/v), glutamine, sodium carbonate) supplemented with 10% FBS, 1 ng/mL EGF, 1 mM CaCl2, penicillin/streptomycin in a humidified 37° C. incubator with 5% $CO_2$. Next day, fresh media is added to cells and cells are treated with 50 µM arachidonic acid to induce sebum lipid synthesis. Untreated cells are used as a control. Cells are cotreated with arachidonic acid and tested active to evaluate the effect of actives on arachidonic acid-induced lipid synthesis. Cells are treated for 24 h. After treatment cells are washed with ice-cold PBS and lipids are stained with 10 ug/mL of nile red for 15 minutes at room temperature, followed by three washes with PBS. Amount of neutral lipids is quantified by measuring fluorescence at Ex485 nm/Em565 nm. The increase in fluorescence is directly proportional to the intracellular levels of neutral sebum lipids in the sebocytes. Results are obtained in triplicate and a p-value s determined. It is expected that use of an *Abutilon indicum* extract at varying concentration will yield decreased concentration of intracellular neutral sebum lipids in the treated cells.

EXAMPLE 12

In Vitro Biopsy

The effect of the inventive abstract on skin equivalent tissues may be evaluated using skin equivalent 3D tissue such as Melanoderm™ FTB (MEL-300-FTB; Mattek, Ashland, Mass.). The composition may be applied either on the tissue topically or in medium basolaterally for a period of days. At the end of the treatment, tissue sections will be fixed with 4% paraformaldehyde, and Fontana-Masson staining wil be conducted. The thickness of the skin equivalent will be measured using a microscope. It is expected that use of an *Abutilon indicum* extract candidate substance at varying concentration will yield thicker skin equivalent 3D tissue than a control preparation.

EXAMPLE 13

Consumer Test Panel Data

A composition such as disclosed in Table 1 is illustrative of a topical composition containing an extract from the ariel portions of the *Abutilon indicum* plant disclosed in Example 1. The compositions may be tested on multiple subjects (panelists) and compared, for instance, to a commercially available topical compositions. As will be appreciated by the practitioner, panelists can be asked to apply the control composition and a prototype to their skin over a period of hours, days, or months, and evaluate the formulations based on a questionnaire. For instance, 45anelists may be asked whether the prototype reduces fine lines, wrinkles, sagging skin, and other conditions due to a progressive degradation of the skin cell growth, proliferation and functionality in the epidermal and dermal layer. The results are expected to demonstrate the improvement of the aesthetic appearance of aging skin in need thereof due to an application of the *Abutilon indicum* extract.

EXAMPLE 14

In Vivo Biopsy

Healthy female Caucasian subjects aged 30-65, with skin type II or III and mild to moderate photo damage, were treated on the dorsal forearm for 3 weeks (3 consecutive rounds of 5×24 hour) under semi-occlusion patches. Test articles including active ingredients, vehicle controls, and retinol were applied in a randomized allocation on 6 sites on each forearm. The application dose was 2 mg/cm². After 3 week treatment, a 2 mm punch biopsy was obtained from each treatment site and fixed in 10% buffered formalin. Tissue samples then embedded in paraffin, sectioned (5 µm thickness), and stained for skin markers after re-hydration.

Analysis of the tissue samples with respect to histology endpoints showed that use of *Abutilon indicum* extract at a 0.33% active concentration in the semi-occlusion patch vehicle formulation yielded a visual score of approximately 0.07 out of a 4 point scale in HE staining (measuring hematoxylin and eosin staining, an indication of viable epidermal thickness and health) with 26% of the subjects showing an improvement; a visual score of 0.45 out of a 4 point scale in M-TC staining (Masson's trichrome staining, assessing total mature fiber-forming collagen in the dermis—mainly Collagen I, Collagen II and Collagen V) with 47% of the subjects showing an improvement; a visual score of 0.09 out of a 4 point scale for pro-Col (measuring new synthesis of Collagen I by skin fibroblasts in the dermis) with 28.1% of the subjects showing an improvement; and a visual score of 0.31 out of a 4 point scale for HA (measuring level of hyaluronic acid in both dermis and epidermis) with 51% of the subjects showing an improvement. Retinol at a active concentration of 0.05% was used as a positive control. Retinol use at a 0.05% active concentration in the semi-occlusion patch vehicle formulation yielded a visual score of approximately 0.56 out of a 4 point scale in HE staining (measuring hematoxylin and eosin staining, an indication of viable epidermal thickness and health) with 63.6% of the subjects showing an improvement; a visual score of 0.6 out of a 4 point scale in M-TC staining (Masson's trichrome staining, assessing total mature fiber-forming collagen in the dermis—mainly Collagen I, Collagen II and Collagen V) with 51.6% of the subjects showing an improvement; a visual score of 0.52 out of a 4 point scale for pro-Col (measuring new synthesis of Collagen I by skin fibroblasts in the dermis) with 51.6% of the subjects showing an improvement; and a visual score of 0.57 out of a 4 point scale for HA (measuring level of hyaluronic acid in both dermis and epidermis) with 50% of the subjects showing an improvement.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for providing a skin benefit to human skin comprising topically applying to an area of the skin in need thereof an effective amount of a water and alcohol extract of *Abutilon indicum*; wherein said skin benefit comprises improvement in pro-collagen and/or collagen production in the skin; wherein said extract is applied to said skin at least once daily for a period of at least four weeks.

2. The method according to claim 1, wherein said skin benefit includes a reduction in fine lines and/or wrinkles.

\* \* \* \* \*